US008710028B2

(12) United States Patent
Watts et al.

(10) Patent No.: US 8,710,028 B2
(45) Date of Patent: Apr. 29, 2014

(54) PHARMACEUTICAL POWDER COMPOSITIONS

(75) Inventors: Peter James Watts, Nottingham (GB); Yu-Hui Cheng, Nottingham (GB); Alan Smith, Nottingham (GB); Jonathan Castile, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 0 days.

(21) Appl. No.: 12/675,306

(22) PCT Filed: Aug. 29, 2008

(86) PCT No.: PCT/GB2008/002949
§ 371 (c)(1),
(2), (4) Date: Feb. 25, 2010

(87) PCT Pub. No.: WO2009/027705
PCT Pub. Date: Mar. 5, 2009

(65) Prior Publication Data
US 2010/0256091 A1    Oct. 7, 2010

(30) Foreign Application Priority Data
Aug. 31, 2007   (GB) .................................. 0716907.1

(51) Int. Cl.
  *A61K 31/55*    (2006.01)
  *A61K 31/70*    (2006.01)
(52) U.S. Cl.
  USPC .............................. 514/55; 514/218; 514/219
(58) Field of Classification Search
  None
  See application file for complete search history.

(56) References Cited

U.S. PATENT DOCUMENTS 6,610,271 B2    8/2003   Wermeling

FOREIGN PATENT DOCUMENTS

| JP | 05017371 A | 1/1993 |
|----|-----------|--------|
| WO | 9605810 A1 | 2/1996 |
| WO | 9830207 A1 | 7/1998 |
| WO | 9901498 A1 | 1/1999 |
| WO | 2005025541 A2 | 3/2005 |
| WO | 2007034032 A1 | 3/2007 |

OTHER PUBLICATIONS

Lim et al., International Journal of Pharmaceutics, 2002, 231, 73-82.*
Wallace, The Lancet, 1997, 349, 222.*
"Definition of derivertive", retrieved from Merriam-Webster online dictionary <<http://www.merriamwebster.com/dictionary/derivative>> on Apr. 6, 2011, 2 pages.*
CAS registry—chitosan glutamate, retrieved on May 31, 2012 from CAS registry, 1 page.*
Benzodiazepine, Wikipedia, the free encyclopedia, pp. 1-21 (Jul. 8, 2007).
Bernkop-Schnurch, A., et al., "Thiolated polymers-thiomers: synthesis and in vitro evaluation of chitosan-2-iminothiolane conjugates," International Journal of Pharmaceutics, 260, pp. 229-237 (2003).
Calvo, P., et al., "Development of positively charged coloidal drug carriers: chitosan-coated polyester nanocapsules and submicron-emulsions," Colliod and Polymer Science, 275: pp. 46-53 (1997).
Carstensen, J. T., Ph.D "Pharmaceutical Principles of Solid Dosage Forms," Technomic, Lancaster, PA, Chapters 2 and 6, (1993).
Cheng, Y., et al., "Intranasal delivery of recombinant human growth hormone (somatropin) in sheep using chitosan-based powder formulations," European Journal of Pharmaceutical Sciences, 26, pp. 9-15, (2005).
Costantino, H., et al., "Intranasal delivery: Physicochemical and therapeutic aspects," International Journal of Pharmaceutics, 337, pp. 1-24, (2007).
Florence, A.T., et al., "Physicochemical Principles of Pharmacy and Pharmaceutical Sciences University of Manchester," School of Pharmacy, 3rd Ed., pp. 357-360 (1998).
Gavini, E., et al., "Nasal administration of Carbamazepine using chitosan microspheres: In vitro/in vivo studies," International Journal of Pharmaceutics, 307: pp. 9-15 (2006).
Gennaro, A., et al., "Remington: The Science and Practice of Pharmacy," University of Sciences in Philadelphia, 20th Ed., Chapter 37, (2000).
Goodman & Gilman's The Pharmacological Basis of Therapeutics, 9th Ed., McGraw-Hill, p. 363 (1996).
Holappa, J., et al., Novel Water-Soluble Quaternary Piperazine Derivatives of Chitosan: Synthesis and Characterization, Macromol. Biosci. 6, pp. 139-144, (2006).
Illum, L., "Nasal drug delivery—possibilities, problems and solutions," Journal of Controlled Release 87, pp. 187-198, (2003).
Illum, L., "Nasal drug delivery: new developments and strategies," Drug Discovery Today, 7(23): pp. 1184-1189, Dec. 2002.
International Search Report and Written Opinion dated Feb. 3, 2009, for PCT/GB2008/002949, 15 pages.
Martin, A., et al., "Physical chemical principles in the Pharmaceutical Sciences," Physical Pharmacy, 4th Ed., Williams & Wilkins, Baltimore, pp. 516-519, (1993).
Shiraishi, S., et al., "Enhancement of Dissolution Rates of Several Drugs by Low-Molecular Chitosan and Alginate," Chem Pharm. Bull., 38(1): pp. 185-187 (1990).
Thanou, M., et al., "N-Trimethylated Chitosan Chloride (TMC) Improves the Intestinal Permeation of the Peptide Drug Buserelin In Vitro (Caco-2 Cells) and In Vivo (Rats)," Pharmaceutical Research, 17(1): pp. 27-31, (2000).
Thanou, M., et al., "Mono-N-Carboxymethyl Chitosan (MCC), a Polyampholytic Chitosan Derivative, Enhances the Intestinal Absorption of Low Molecular Weight Heparin Across Intestinal Epithelia In Vitro and in Vivo," Journal of Pharmaceutical Sciences, 90(1): pp. 38-46, Jan. 2001 (published online Nov. 1, 2000).

(Continued)

*Primary Examiner* — Elli Peselev
(74) *Attorney, Agent, or Firm* — Panitch Schwarze Belisario & Nadel LLP

(57) ABSTRACT

A powder composition for intranasal delivery includes a benzodiazepine drug and chitosan, a salt of chitosan, a derivative of chitosan or a salt of a derivative of chitosan.

9 Claims, 1 Drawing Sheet

(56) References Cited

OTHER PUBLICATIONS

Washington, C., "Particle Size Analysis in Pharmaceutics and Other Industries Theory and Practice," Ellis Horwood, 7 pages (Title Pages and Table of Contents) (1992).

Office Action issued May 7, 2013 in JP Application No. 2010-522448.

Bones et al, "Using Environmental Analytical Data to Estimate Levels of Community Consumption of Illicit Drugs and Abused Pharmaceuticals," Journal of Environmental Monitoring, vol. 9, pp. 701-707 (2007).

General information on "Gentamicin" from the Veterinary Substances Data Base (May 19, 2011).

Portero et al, "Effect of chitosan and chitosan glutamate enhancing the dissolution properties of the poorly water soluble drug nifedipine," International Journal of Pharmaceutics, vol. 175, pp. 75-84 (1998).

Martindale, "The complete drug reference", Thirty-Second Edition, 1999, pp. 212 and 661.

Stegemann et al, "When Poor Solubility Becomes an Issue: From Early Stage to Proof of Concept," originally published in the European Journal of Pharmaceutical Sciences, 2007, vol. 31, pp. 249-261, available at http://smtp.capsugel.com/media/library/when-poor-solubility-becomes-an-issue-from-early-stage-to-proof-of-concept.pdf.

O'Regan et al, "Nasal rather than rectal benzodiazepines in the management of acute childhood seizures?", Dev. Med. Child Neurol., 1996, vol. 38, pp. 1037-1045 (abstract only).

* cited by examiner

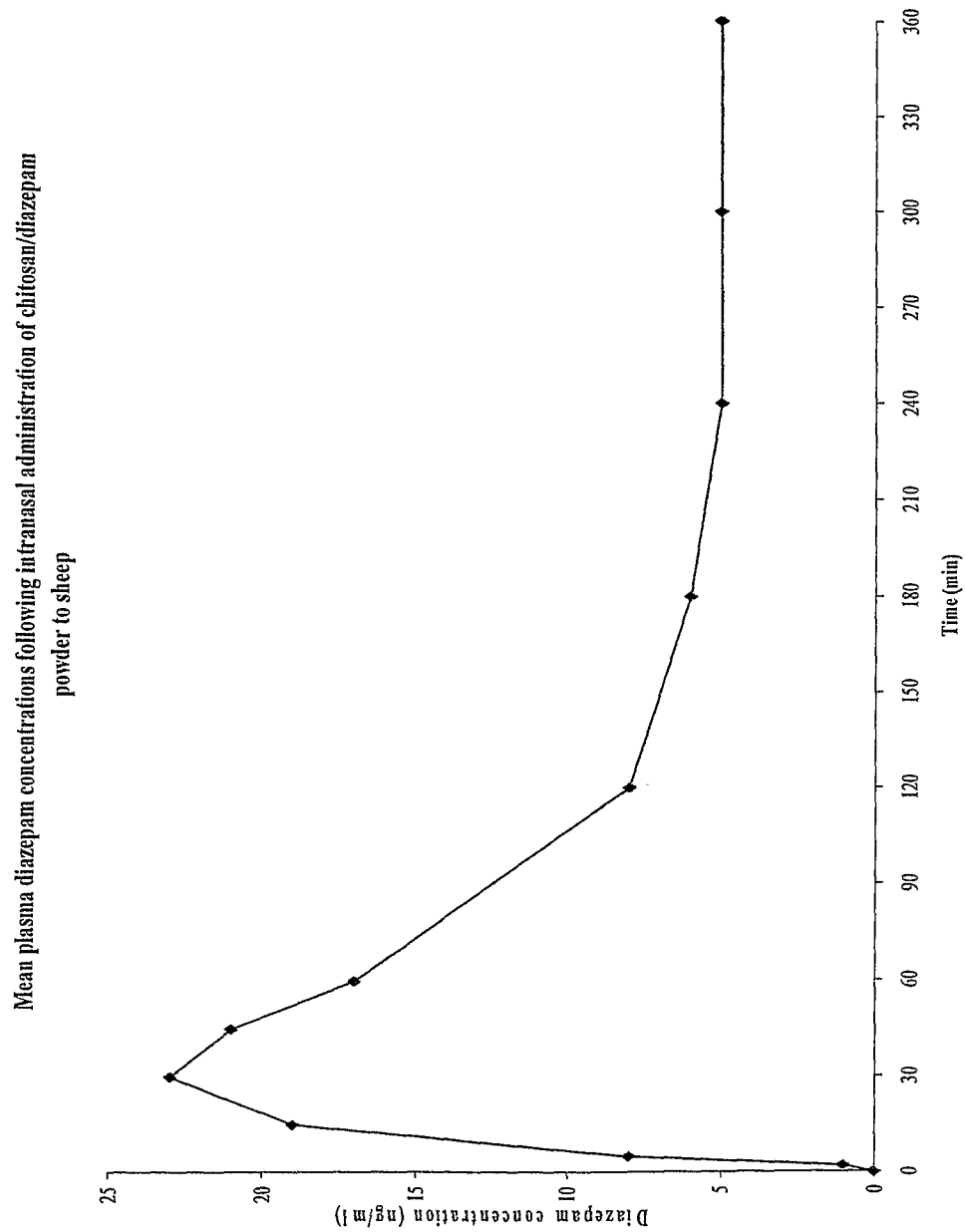

PHARMACEUTICAL POWDER COMPOSITIONS

CROSS-REFERENCE TO RELATED APPLICATIONS

This application is a Section 371 of International Application No. PCT/GB2008/002949, filed Aug. 29, 2008, which was published in the English language on Mar. 5, 2009, under International Publication No. WO 2009/027705 A1 and the disclosure of which is incorporated herein by reference.

BACKGROUND OF THE INVENTION

This invention relates to pharmaceutical compositions for the nasal administration of benzodiazepine drug compounds. More particularly, this invention relates to pharmaceutical compositions for nasal administration which are in the form of a powder and comprise a benzodiazepine drug compound and chitosan.

The nasal route of drug delivery can afford rapid absorption of drugs into the blood circulation. In some cases absorption of almost the whole dose can be achieved and the pharmacokinetics can be similar to those achieved for intravenous administration. Such rapid and effective drug delivery can be useful in the treatment of crisis situations such as pain (including breakthrough pain, headache), migraine, anxiety, convulsions, impotence and nausea.

A class of compounds of interest for nasal delivery is the benzodiazepines. These lipophilic drugs act on the central nervous system to cause sedation, hypnosis, decreased anxiety, muscle relaxation, anterograde amnesia and anticonvulsant actions and are widely used in medicine. Conditions which they can be used to treat include anxiety, epilepsy, insomnia, alcohol dependence, muscular disorders and mania. These drugs can also be used in premedication procedures and in veterinary practices. Examples of benzodiazepine drugs include but are not limited to alprazolam, chlordiazepoxide, clonazepam, clorazepate, diazepam, estazolam, flurazepam, halazepam, lorazepam, midazolam, nitrazepam, oxazepam, prazepam, quazepam, temazepam, bromazepam, flunitrazepam, triazolam, bentazepam, brotizolam, clotiazepam, delorazepam, ethyl loflazepate, etizolam, fludiazepam, ketozolam, loprazolam, lormetazepam, nordazepam, mexazolam, nimetazepam, pinazepam and tetrazepam. The structures of some of these benzodiazepines can be found in Goodman and Gilman's The Pharmacological Basis of Therapeutics, 9th edition, McGraw Hill (1996), page 363.

The listing or discussion of an apparently prior-published document in this specification should not necessarily be taken as an acknowledgement that the document is part of the state of the art or is common general knowledge.

The preferred means of delivering drugs for systemic action by the intranasal route is using an aqueous solution formulation. However, lipophilic (non-polar) drugs such as benzodiazepines typically have low aqueous solubility and hence present a significant challenge when designing a nasal formulation.

Drugs may also be delivered intranasally in the form of a powder. However, powder formulations are typically not suitable for intranasal delivery of a lipophilic, poorly-soluble drug since the volume of liquid in the nasal cavity for dissolution is small and the residence time of the formulation in the nasal cavity is low. Consequently, the time available for drug dissolution and therefore absorption, is limited.

The present inventors have surprisingly found that lipophilic, poorly water soluble drugs such as benzodiazepines can be successfully administered intranasally if delivered in the form of a powder containing chitosan. By successfully administered, we mean that therapeutically effective amounts of drug can be absorbed into the systemic circulation.

Chitosan is a bioadhesive cationic biopolymer comprising glucosamine and N-acetyl glucosamine. Chitosan has been shown to improve the systemic bioavailability of certain drug compounds across mucosal surfaces such as the nasal cavity (see Illum, Drug Discovery Today 7, 1184-1189, 2002).

There are number of reports on the use of chitosan to improve the intranasal absorption of polar small molecules such as morphine and peptides such as calcitonin and leuprolide (Ilium, J. Control. Rel., 87, 187-198, 2003) and proteins such as human growth hormone (Cheng et al, Eur. J. Pharm. Sci., 26, 9-15, 2005).

The use of chitosan in powder form to enhance the absorption of lipophilic drugs such as of benzodiazepine drugs has not been reported.

BRIEF SUMMARY OF THE INVENTION

The invention provides a powder composition for intranasal delivery comprising a benzodiazepine drug compound and chitosan, a salt of chitosan, a derivative of chitosan or a salt of a derivative of chitosan.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 illustrates the mean plasma diazepam concentrations following intranasal administration of chitosan/diazepam powder to sheep (see Example 9).

DETAILED DESCRIPTION OF THE INVENTION

Chitosan is prepared by the deacetylation of chitin. In accordance with the present invention, the degree of deacetylation, which represents the proportion of N-acetyl groups which have been removed through deacetylation, should preferably be in the range of from about 40 to about 97%, more preferably in the range of from about 60 to about 96% and most preferably be in the range of from about 70 to 95%.

The chitosan should preferably have a molecular weight of from about 5,000 to about 1,000,000 Da, more preferably of from about 10,000 to about 800,000 Da and most preferably of from about 15,000 to about 600,000 Da or from 30,000 or 50,000 to about 600,000 Da.

By the term "chitosan" we include all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation) and pharmaceutically acceptable organic or inorganic salts. Suitable salts include, but are not limited to nitrate, phosphate, acetate, hydrochloride, lactate, citrate or glutamate. Preferred salts are chitosan glutamate and chitosan hydrochloride. The most preferred salt is chitosan glutamate.

Chitosan derivatives and their salts are also suitable for use in this invention. Chitosan derivatives may be prepared by bonding moieties to the hydroxyl or amino groups of chitosan and may confer the polymer with changes in properties such as solubility characteristics, charge density and mucoadhesiveness. For example, suitable chitosan derivatives prepared by bonding moieties to the hydroxyl groups of chitosan include esters, ethers or other derivatives formed by bonding acyl and/or alkyl groups with the hydroxyl groups. Examples include O-alkyl ethers of chitosan and O-acyl esters of chitosan. Other examples of chitosan derivatives include carboxymethyl chitosan (e.g. Thanou et al, J. Pharm. Sci., 90, 38-46, 2001), trimethylchitosan (e.g. Thanou et al, Pharm. Res., 17-27-31, 2000), thiolated chitosans (e.g. Bernkop-Schnurch et al, Int. J. Pharm., 260, 229-237, 2003) and piperazine derivatives (e.g. WO2007/034032 and Holappa et al, Macromol. Biosci., 6, 139-144, 2006). Chitosan derivatives for use in the invention also include those modified by conjugation with polyethylene glycol, for example as described in WO 99/01498. Suitable derivatives include those that are disclosed in Roberts, Chitin Chemistry, MacMillan Press Ltd., London (1992).

It is preferable that the chitosan, chitosan derivative or salt used in the present invention is water soluble. By "water soluble" we mean that the chitosan, chitosan derivative or salt dissolves in water at an amount of at least 10 mg/ml at room temperature and atmospheric pressure.

Chitosans suitable for use in the present invention may be obtained from various sources, including Primex, Iceland; NovaMatrix, Norway; Cognis, Germany; and Meron Biopolymers, India.

Particularly preferred chitosan compounds that may be mentioned include chitosan glutamate (available, for example, as Protasan UPG213 from NovaMatrix, Drammen, Norway).

This invention can be applied to any benzodiazepine compound. Examples of benzodiazepine compounds include, but are not limited to, alprazolam, chlordiazepoxide, clonazepam, clorazepate, diazepam, estazolam, flurazepam, halazepam, lorazepam, midazolam, nitrazepam, oxazepam, prazepam, quazepam, temazepam, bromazepam, flunitrazepam, triazolam, bentazepam, brotizolam, clotiazepam, delorazepam, ethyl loflazepate, etizolam, fludiazepam, ketozolam, loprazolam, lormetazepam, nordazepam, mexazolam, nimetazepam, pinazepam and tetrazepam.

A preferred group of benzodiazepine drugs for use in this invention are diazepam (7-chloro-1,3-dihydro-1-methyl-5-phenyl-2H-1,4-benzodiazepin-2-one), lorazepam (7-chloro-5-(2-chlorophenyl)-1,3-dihydro-3-hydroxy-2H-1,4-benzodiazepin-2-one), clonazepam (5-(2-chlorophenyl)-1,3-dihydro-7-nitro-2H-1,4-benzodiazepin-2-one) and midazolam (8-chloro-6-(2-fluorophenyl)-1-methyl-4H-imidazo[1,5-a][1,4]benzodiazepine).

In one aspect of the invention any benzodiazepine compound may be used provided that it is not clonazepam. For example, in accordance with this invention compositions containing clonazepam do not comprise type A, cationic gelatin.

Methods of formulating drug substances for administration in a powder form are well known to those skilled in the art. Any such method may be used to formulate the composition of the present invention. For example, the benzodiazepine drug may be formulated as a blend of drug powder with other ingredients, as granules or microspheres or as a freeze-dried powder.

The simplest form of the powder compositions of the invention is a blend of benzodiazepine drug and chitosan. The compositions of the invention may optionally comprise one or more inert ingredients which are standard in the art. Such ingredients include, but are not limited to, diluents such as calcium phosphate, lactose, dextrose, sugars such as sucrose and dextrose, polyols such as mannitol and sorbitol, and celluloses such as microcrystalline cellulose; glidants such as colloidal silica; lubricants such as magnesium stearate and hydrogenated vegetable oil; surfactants such as polysorbates; sweeteners such as aspartame and saccharine; and flavours.

For preparing a substantially uniform powder blend on a small scale, a pestle and mortar and/or sieve may be appropriate whereas mechanical mixers are required for larger scale manufacture. There are numerous types of mixer available and these are widely described in the literature, for example Chapter 37, Remington: The Science and Practice of Pharmacy, 20th Edition, Lipincott, Williams and Wilkins, Baltimore, 2000. By "substantially uniform" we mean the drug is evenly distributed within the formulation such that if the theoretical weight of powder in which the drug dose is contained is analysed for drug content the result will be in the range 80-120% of the nominal amount i.e. if 5 mg of drug is theoretically contained within 10 mg of powder formulation, the drug distribution will be considered substantially uniform if the assayed amount of drug in 10 mg of powder is in the range 4-6 mg.

Although the formation of a powder blend is the simplest approach, there are a number of other methods that may be used. For example, methods such as granulation, microencapsulation and lyophilisation can be used and are particularly useful when there is a need to control particle size and for uniformity of drug distribution within the composition. Other suitable methods of formulation include spray drying and super critical fluid processes. Of these other methods, granulation is preferred since it is of relatively low complexity and an economical process.

In one aspect, the compositions of the invention comprise granules of one or more ingredients of the composition. Granules are agglomerates of smaller particles and may be produced by techniques well known to those skilled in the art such as wet granulation, dry granulation (slugging), extrusion/spheronisation, fluid bed granulation and spray congealing. In addition to the drug and chitosan, other ingredients incorporated into the granules may include the inert ingredients such as diluents, glidants, lubricants, sweetener and flavours, as described earlier. In addition, granules may include binders such as povidone (polyvinylpyrrolidone), methylcellulose, polyethylene glycol, gelatin and acacia and disintegrants such as starch, croscarmellose and crospovidone. It is possible for compositions of the invention to contain type A cationic gelatin. However, this is not preferred and in a particular aspect the present invention provides compositions which do not comprise type A cationic gelatin.

In a wet granulation process, a solution of a binding agent in an aqueous or organic solvent (the granulating solvent) is mixed into the solid ingredients (e.g. drug and chitosan) to form a homogeneous mass. The mass is passed through a coarse mesh and the aqueous or organic solvent removed by evaporation/drying to produce granules. The granules may then, if required, be further milled and sieved to produce particles of the desired size.

The binding agent is typically dissolved in the granulating solvent, alternatively it may added in dry form to the powder mixture and the solvent added to the powder blend to form the homogeneous mass. Further details on the process of granulation may be found in the literature, for example Chapter 6, Pharmaceutical Principles of Solid Dosage Forms, J. T. Carstensen, Technomic, Lancaster, Pa., 1993.

It is preferable that benzodiazepine drug and chitosan are contained within the same granule, however, other configurations are possible. Examples of other configurations include a blend of chitosan (non-granule form) and drug granules, a blend of chitosan granules and benzodiazepine drug granules; and a blend of benzodiazepine drug powder (non-granule form) and chitosan granules. In all cases other ingredients, as described earlier, may be added as necessary to the granule and/or non-granule component of the composition.

A substantially uniform powder composition may also be prepared by a process involving lyophilisation (freeze-drying). A solution or suspension of drug and chitosan is prepared, including other inert ingredients as required. The solution is frozen and lyophilised to leave either a powder as a plug or in a dispersed (free-flowing) form. The particle size of powders produced by freeze drying is sometimes heterogeneous and poorly defined. Thus, the lyophilised powder may undergo a process to produce particles of a well defined size. Methods for reduction of particle size, which may also be applied to the granule compositions, are well known to those skilled in the art. The preferred method for reducing the particle size of the compositions is by milling and/or sieving. There are numerous types of mill available and these are widely described in literature references, such as in Chapter 2, Pharmaceutical Principles of Solid Dosage Forms, J. T. Carstensen, Technomic, Lancaster, Pa., 1993 and Chapter 37, Remington: The Science and Practice of Pharmacy, 20th Edition, Lipincott, Williams and Wilkins, Baltimore, 2000.

The compositions of the invention may be in the form of microspheres. Methods for preparation of microspheres are well known to those skilled in the art and include, but are not limited to, spray drying, interfacial polymerisation, coarcervation/phase separation and solvent evaporation. Methods for producing microspheres are described in, for example, Physicochemical Principles of Pharmacy, $3^{rd}$ Edition, pages 357 to 360, A T Florence and D Attwood, Macmillan, London, 1998 and Physical Pharmacy, $4^{th}$ Edition, pages 516 to 519, A Martin, Wilkins and Wilkins, Baltimore, 1993. The microspheres may alternatively be produced using the methods described in WO98/30207 and the documents cited therein.

In addition to a benzodiazepine drug compound and chitosan, a salt of chitosan, a derivative of chitosan or a salt of a derivative of chitosan, the microspheres used in the present invention may include ingredients that are known in the art to be suitable to be included in microspheres. Such ingredients include, but are not limited to, starches, dextrans, gelatin, albumin, collagen, hyaluronic acid, lactose, sucrose, dextrose, mannitol, methacrylate copolymers such as the Eudragit® polymers (Degussa, Germany), celluloses such as methylcellulose, and polyesters such as poly(lactide-co-glycolide). It is possible for microspheres of the invention to contain type A cationic gelatin. However, this is not preferred and in a particular aspect the present invention provides microspheres which do not comprise type A cationic gelatin.

The powder compositions of the present invention preferably have a benzodiazepine drug content of from about 10 to about 90% by weight of the composition, more preferably from about 15 to about 85% by weight and most preferably from about 20 to about 80% by weight. The remainder of the powder composition comprises chitosan and, optionally, other ingredients, as described earlier. In the absence of other ingredients, the chitosan content of the powder composition is preferably 10 to about 90% by weight of the composition, more preferably from about 15 to about 85% and most preferably from about 20 to about 80%.

One or more additional (inert) ingredients mentioned above may be included preferably up to 20% by weight of the composition (based on the total weight of any additional (inert) ingredient(s) included in the composition), more preferably up to 15% by weight and most preferably up to 10% by weight. When other such ingredients are included in the compositions of the invention, they may simply be added to the compositions comprising the drug and chitosan in an amount as defined above. Alternatively, they may replace a portion of the chitosan, a salt of chitosan, a derivative of chitosan or a salt of a derivative of chitosan.

A preferred composition of the invention comprises granules comprising a benzodiazepine (for example a benzodiazepine such as diazepam, midazolam or lorazepam) chitosan (for example the glutamate salt of a chitosan) and a binder (for example povidone). Preferred proportions of these three components are provided in the table below:

|  | Composition (% w/w) | | |
| --- | --- | --- | --- |
|  | Preferred | More preferred | Most preferred |
| Benzodiazepine | 2-90 | 5-85 | 10-80 |
| Chitosan | 9-97 | 14-94 | 19-89 |
| Binder | 0.1-10 | 0.3-7.5 | 0.5-5 |

Two examples of preferred diazepam compositions of the inventions comprise granules comprising from 45 to 55% w/w diazepam, from 42 to 54% w/w chitosan glutamate and from 1 to 3% w/w povidone (binder) and granules comprising from 70 to 80% w/w diazepam, from 17 to 29% w/w chitosan glutamate and from 1 to 3% w/w povidone (binder).

An example of a preferred lorazepam-containing composition of the invention comprises granules comprising from 20 to 30% w/w lorazepam, from 67 to 79% w/w chitosan glutamate and from 1 to 3% w/w povidone (binder).

An example of a preferred midazolam-containing composition of the invention comprises granules comprising from 35 to 45% w/w midazolam, from 52 to 64% w/w chitosan glutamate and from 1 to 3% w/w povidone (binder).

An example of a preferred clonazepam-containing composition of the invention comprises granules comprising from 10 to 50% w/w clonazepam, from 47 to 89% w/w chitosan glutamate and from 1 to 3% w/w povidone (binder).

The present invention provides a nasal drug delivery device or a dose cartridge for use in a nasal drug delivery device loaded with a composition of the invention.

The powder composition of the invention is preferably administered to the patient in aerosolised form. For example, energy from patient inhalation (sniffing) may be used to aerosolise the powder into the nasal cavity (passive delivery device) or where the delivery device itself may provide the aerosolisation energy, such as via compressed air (active delivery device). An example of the former device is manufactured by Pfeiffer, Radolfzell, Germany and an example of the latter is the "Monopowder" manufactured by Valois, Marly-le-Roi, France or the "UniDose" manufactured by Bespak, Milton Keynes, UK. An active device is preferred if the drug is to be administered to an incapacitated (e.g. unconscious) patient.

The particle size distribution of the compositions needs to be such that they are efficiently aerosolised from the delivery device and evenly distributed across the absorptive surface of the nasal cavity. Additionally, the drug also needs to rapidly dissolve when deposited in the nasal cavity. These properties are more readily achieved by smaller particles. However, the number of very small particles (below 10 μm in diameter) needs to be controlled in order to minimise deposition within the lungs. There are a number of methods for measuring the particle size distribution of powders, including sieve analysis, light microscopy and laser diffraction (see C. Washington, Particle size analysis in pharmaceutics and other industries, Ellis Horwood, Chichester, 1992). The particle size distribution may be measured on the bulk powder or on the powder as it is emitted from the device. The mean particle size (diameter) of the powder is preferably in the range 0.012-0.6 mm, more preferably in the range 0.014-0.5 mm and most preferably in the range 0.016-0.4 mm. The percentage of particles (by volume) below 10 μm is preferably less than 25%, more preferably less than 20% and most preferably less than 15%.

The present invention provides processes for preparing the compositions of the invention. These processes are described above.

The compositions of the invention can be used to treat and/or prevent certain disorder conditions or diseases of the central nervous system and in particular can be used to cause sedation, hypnosis, decreased anxiety, muscle relaxation, anterograde amnesia and anticonvulsant actions. They can also be used to treat and/or prevent anxiety, epilepsy, insomnia, alcohol dependence, muscular disorders and mania. Thus, the present invention provides a method of administering a benzodiazepine drug compound, particularly a compound as listed above, to a patient in need thereof, for example for the prevention or treatment of the disorders, conditions or diseases set out above and/or to induce the effects set out above, which comprises the intranasal administration of a composition as defined above to the patient.

As used herein, we use the term "patient" to refer to both human and non-human animals. The invention is particular suitable for use in the treatment of humans and animals such as dogs.

The present invention also provides the use of a benzodiazepine drug, such as a drug as listed above and chitosan in the manufacture of a medicament for nasal administration to a patient in need of the drug. Such a medicament may be for the treatment and/or prevention of disorders, conditions or diseases of the central nervous system and/or to induce sedation, hypnosis, decreased anxiety, muscle relaxation, anterograde amnesia and anticonvulsant actions or to treat anxiety, epilepsy, insomnia, alcohol dependence, muscular disorders or mania.

The present invention also provides powder compositions comprising a benzodiazepine drug compound and chitosan and optionally additional ingredients as defined above for nasal delivery for use in treating and/or prevention of disorders, conditions or diseases of the central nervous system and/or to induce sedation, hypnosis, decreased anxiety, muscle relaxation, anterograde amnesia and anticonvulsant actions or to treat anxiety, epilepsy, insomnia, alcohol dependence, muscular disorders or mania.

The invention is illustrated by the following non-limiting Examples.

EXAMPLE 1

Powder Blend Comprising 50% w/w Diazepam and 50% w/w Chitosan Glutamate 400 mg of diazepam (Cambrex, Italy) and 400 mg of chitosan glutamate (Protasan UPG213, NovaMatrix, Norway) were weighed and transferred to a mortar and pestle. After gently mixing together the two components the powder was passed through a 90 μm sieve. The sieved powder was transferred to a glass bottle, capped and then mixed using a Turbula T2C mixer (Willy Bachofen, Switzerland) at speed setting 2 for 30 minutes.

EXAMPLE 2

Granules Containing 50% w/w Diazepam, 48.5% w/w Chitosan Glutamate and 1.5% w/w Polyvinyl Pyrrolidone 500 mg of diazepam and 485 mg of chitosan glutamate were weighed and transferred to a beaker. 15 mg of polyvinyl pyrrolidone (Kollidon 30, BASF, Germany) was dissolved in 1 ml of ethanol (Fisher, UK) and thoroughly mixed using a spatula. The solvent was evaporated in a fume cupboard, and then in an oven at 40° C. The dry granules were passed through a 150 μm sieve then over a 25 μm sieve using the Fritsch A3 vibratory sieve shaker at amplitude setting 2.5 for 20 minutes. The granules between 25 and 150 μm were collected.

EXAMPLE 3

Granules Containing 75% w/w Diazepam, 23.5% w/w Chitosan Glutamate and 1.5% w/w Polyvinyl Pyrrolidone 375 mg of diazepam and 117.5 mg of chitosan glutamate were weighed and transferred to a beaker. 7.5 mg of polyvinyl pyrrolidone was dissolved in 0.5 ml of ethanol (Fisher, UK) and thoroughly mixed using a spatula. The solvent was evaporated in a fume cupboard, then in an oven at 40° C. The dry granules were passed through a 150 μm sieve then over a 25 μm sieve using the Fritsch A3 vibratory sieve shaker at amplitude setting 2.5 for 20 minutes. The granules between 25 and 90 μm were collected.

EXAMPLE 4

Granules Containing 20% w/w Midazolam, 77% w/w Chitosan Glutamate and 3% w/w Polyvinyl Pyrrolidone 400 mg of midazolam (Sigma) was weighed into a glass beaker and 60 mg of polyvinyl pyrrolidone (Kollidon 30, BASF, Germany) added. 5 ml of ethanol (Sigma) was added to the beaker and the contents stirred until dissolved. 1540 mg of chitosan glutamate was added to the beaker and mixed into the midazolam/polyvinyl pyrrolidone solution. The beaker and contents were placed into a fume cupboard and the majority of ethanol was allowed to evaporate. The beaker contents were then transferred to an oven at 40° C. and dried until a constant weight was reached. The dried material was passed through a 90 μm mesh size sieve and the granules collected.

EXAMPLE 5

Formulation Comprising Chitosan Granules Blended with Diazepam

A blend of diazepam and chitosan granules was prepared using a combination of blending and granulation processes. Placebo granules with a 25-150 μm particle size and containing 97% w/w chitosan and 3% w/w PVP were prepared by the process described in Example 2. 300 mg of diazepam was then blended with 300 mg of the placebo granules in a 20 ml vial using a Turbula T2C mixer at speed setting 2 for 30 minutes.

EXAMPLE 6

Freeze-Dried Powder Comprising 50% w/w Chitosan Glutamate and 50% w/w Diazepam 100 mg of chitosan glutamate was weighed into 10 ml volumetric flask and dissolved in approximately 8 ml of water. The flask contents were then made up to volume with water. 100 mg of diazepam was weighed into a small glass beaker and chitosan solution added dropwise while stirring to form a suspension. The chitosan suspension was transferred to a 50 ml conical flask and, while gently agitating, the flask was immersed into liquid nitrogen to freeze the contents. The flask is transferred into a freeze drier and lyophilised for 48 hours. The resulting cake of solid material was passed through a 0.2 mm sieve and particles suitable for nasal administration collected.

EXAMPLE 7

Freeze-Dried Powder Comprising 50% w/w Diazepam, 35% w/w Chitosan Glutamate and 15% w/w Mannitol 100 mg of chitosan glutamate and 43 mg of mannitol (Gattefosse, France) were weighed into a 10 ml volumetric flask and dissolved in approximately 8 ml of water. The flask contents were then made up to volume with water. 143 mg of diazepam was weighed into a small glass beaker and chitosan/mannitol solution added dropwise while stirring to form a suspension. The chitosan suspension was transferred to a 50 ml conical flask and, while gently agitating, the flask was immersed into liquid nitrogen to freeze the contents. The flask was transferred into a freeze drier and lyophilised for 48 hours. The resulting cake of solid material was passed through a 0.2 mm sieve and particles suitable for nasal administration collected.

EXAMPLE 8

Powder Containing 20% w/w Lorazepam and 80% w/w Chitosan Hydrochloride 100 mg of lorazepam (Sigma) and 400 mg of chitosan hydrochloride (Protasan UP CL 213, NovaMatrix, Norway) are weighed and transferred to a mortar and pestle. After gently mixing together the two components the powder is passed through a 90 μm sieve. The sieved powder is transferred to a glass bottle, capped and then mixed using a Turbula T2C mixer (Willy Bachofen, Switzerland) at speed setting 2 for 30 minutes.

EXAMPLE 9

Evaluation of Pharmacokinetic Performance of Diazepam Powder Formulation in Sheep The pharmacokinetic performance of the formulation described in Example 2 was evaluated following intranasal administration to sheep (n=6). For the purpose of determining absolute bioavailability an intravenous injection of diazepam was administered (diazepam injection, 5 mg/ml, Wockhardt UK Ltd).

The intranasal powder was administered at a dose of 0.5 mg/kg, equivalent to 0.25 mg/kg diazepam (equivalent to approximately 10 mg per animal) and divided equally between nostrils. The powder was administered using oral/nasal tracheal tubes (one tube per nostril). The intravenous control was administered at the same diazepam dose. Blood samples were collected at 0 (pre-dose) and post-dose at 2, 5, 15, 30, 45, 60, 120, 180, 240, 300 and 360 minutes. The blood samples were immediately dispensed into a 5 ml lithium heparin (LH) tube prior to plasma separation by centrifugation. Plasma samples were stored frozen at −80° C. awaiting analysis.

Plasma samples were analysed for diazepam content using LC-MS/MS. Pharmacokinetic parameters were calculated from the diazepam plasma concentration data and are provided in the table below. The plasma concentration vs. time profile for the nasal powder formulation is provided in FIG. 1. Diazepam was rapidly and efficiently absorbed from the powder formulation.

| PK parameter (mean, n = 5) | Nasal powder | I.V. injection |
|---|---|---|
| $C_{max}$ (ng/ml) | 23 | 460 |
| $T_{max}$ (min) | 30 | 2 |
| Absolute bioavailability (%) | 33 | — |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A composition in the form of a mixture of powders or granules, the composition comprising a benzodiazepine drug and a salt of chitosan, a derivative of chitosan that has been formed by bonding acyl or alkyl groups with hydroxyl groups of the chitosan, or a salt of the derivative of chitosan, but not comprising type A cationic gelatin, wherein the mean particle size of the powder is 0.012 mm to 0.6 mm and the chitosan has a molecular weight of 10,000 to 800,000 Da, and wherein the salt of chitosan, the derivative of chitosan or the salt of a derivative of chitosan has a solubility in water of at least 10 mg/ml at room temperature and atmospheric pressure, such that when the composition is intranasally administered to a subject, a therapeutically effective amount of the benzodiazepine drug is absorbed into the subject's systemic circulation.

2. A composition according to claim 1, wherein the drug is alprazolam, chlordiazepoxide, clonazepam, clorazepate, diazepam, estazolam, flurazepam, halazepam, lorazepam, midazolam, nitrazepam, oxazepam, prazepam, quazepam, temazepem, bromazepam, flunitrazepam, triazolam, bentazepam, brotizolam, clotiazepam, delorazepam, ethyl loflazepate, etizolam, fludiazepam, ketozolam, loprazolam, lormetazepam, nordazepam, mexazolam, nimetazepam, pinazepam or tetrazepam.

3. A composition according to claim 2, wherein the drug is diazepam, lorazepam, clonazepam or midazolam.

4. A composition according to claim 1, wherein the chitosan has a molecular weight of from about 50,000 to about 600,000 Da.

5. A composition according to claim 1 comprising chitosan glutamate.

6. A composition according to claim 1, which is a freeze-dried powder or comprises granules.

7. A composition according to claim 4, which comprises granules, wherein the granules comprise the drug and the salt of chitosan, the derivative of chitosan or the salt of a derivative of chitosan.

8. A method of inducing sedation, hypnosis, decreased anxiety, muscle relaxation, anterograde amnesia or an anticonvulsant action in a patient in need thereof, which method comprises intranasally administering to the patient a therapeutically effective amount of a composition as defined in claim 1.

9. A method of treating anxiety, epilepsy, insomnia, alcohol dependence, muscular disorders or mania in a patient in need thereof, which method comprises intranasally administering to the patient a therapeutically effective amount of a composition as defined in claim 1.

* * * * *